(12) United States Patent
Penninger et al.

(10) Patent No.: US 9,138,173 B2
(45) Date of Patent: Sep. 22, 2015

(54) SYSTEM FOR BED AND PATIENT MOBILITY DEVICE INTEROPERABILITY

(75) Inventors: Jason Penninger, Indianapolis, IN (US); Christopher R. O'Keefe, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 551 days.

(21) Appl. No.: 13/242,312

(22) Filed: Sep. 23, 2011

(65) Prior Publication Data

US 2013/0076517 A1 Mar. 28, 2013

(51) Int. Cl.
*G08B 23/00* (2006.01)
*A61B 5/11* (2006.01)
*A61H 3/00* (2006.01)
*A61G 7/018* (2006.01)
*A61G 7/05* (2006.01)
*A61G 7/10* (2006.01)

(52) U.S. Cl.
CPC .............. *A61B 5/1115* (2013.01); *A61G 7/018* (2013.01); *A61G 7/05* (2013.01); *A61G 7/108* (2013.01); *A61H 3/00* (2013.01); *A61G 2007/0527* (2013.01); *A61G 2203/36* (2013.01); *A61G 2203/80* (2013.01); *A61H 2201/5061* (2013.01); *A61H 2201/5064* (2013.01); *A61H 2201/5097* (2013.01)

(58) Field of Classification Search
None
See application file for complete search history.

(56) References Cited

U.S. PATENT DOCUMENTS

| | | | |
|---|---|---|---|
| 5,794,639 | A | 8/1998 | Einbinder |
| 5,802,640 | A * | 9/1998 | Ferrand et al. ................... 5/617 |
| 6,208,250 | B1 * | 3/2001 | Dixon et al. ............... 340/573.1 |
| 6,917,293 | B2 * | 7/2005 | Beggs ......................... 340/573.1 |
| 7,562,883 | B2 | 7/2009 | Livengood et al. |
| 2002/0070867 | A1 * | 6/2002 | Conway et al. ............ 340/573.1 |
| 2006/0024020 | A1 * | 2/2006 | Badawy .......................... 386/46 |
| 2011/0046498 | A1 * | 2/2011 | Klap et al. .................... 600/534 |
| 2011/0234406 | A1 * | 9/2011 | Young et al. ............... 340/573.1 |
| 2013/0197375 | A1 * | 8/2013 | Heise et al. .................... 600/484 |

OTHER PUBLICATIONS

U.S. Appl. No. 61/346,506, filed May 20, 2010, Green Button for the Conservation of Energy, Assignee—Hill-Rom Services, Inc.
U.S. Appl. No. 12/892,977, filed Sep. 29, 2010, Upper body Support Assembly, Assignee—Hill-Rom Services, Inc.

* cited by examiner

*Primary Examiner* — Curtis King
(74) *Attorney, Agent, or Firm* — Kenneth C. Baran (57) ABSTRACT

A system for interoperability of a person support apparatus and various patient mobility devices are disclosed. The system allows for communication between the person support apparatus and various patient mobility devices.

30 Claims, 6 Drawing Sheets

SYSTEM FOR BED AND PATIENT MOBILITY DEVICE INTEROPERABILITY

BACKGROUND

The subject matter herein is directed generally to a system for bed and patient mobility device interoperability. A need exists for interaction between patient support apparatus and patient mobility devices.

BRIEF SUMMARY

One embodiment of the current disclosure comprises a person support apparatus, a controller configured to receive signals to determine weight supported by said person support apparatus and a motion sensor in communication with said controller.

Another embodiment of the current disclosure comprises a person support apparatus, a controller configured to receive signals to determine weight supported by said person support apparatus and a person support device configured to monitor weight supported by said person support device and in communication with said controller.

Yet another embodiment of the current disclosure comprises a method comprising the steps of monitoring change in weight supported by a person support apparatus, determining change in weight supported by a person support device and modifying an alarm.

Another embodiment of the current disclosure comprises a method comprising the steps of monitoring change in weight supported by a person support apparatus, monitoring motion in a predetermined range and modifying an alarm based on motion in a predetermined range.

BRIEF DESCRIPTION OF THE DRAWINGS

The accompanying drawings incorporated in and forming a part of the specification illustrate several aspects of the claimed subject matter and, together with the description, serve to explain the principles of the claimed subject matter. In the drawings:

DETAILED DESCRIPTION

The embodiments of the claimed subject matter and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments, even if not explicitly stated herein. The examples used herein are intended merely to facilitate an understanding of ways in which the disclosed subject matter may be practiced. Accordingly, the examples and embodiments herein should not be construed as limiting the scope of the claimed subject matter. Moreover, it is noted that like reference numerals represent similar parts throughout the several views of the drawings.

It is understood that the subject matter claimed is not limited to the particular methodology, protocols, devices, apparatus, materials, applications, etc., described herein, as these may vary. It is also to be understood that the terminology used herein is used for the purpose of describing particular embodiments only, and is not intended to limit the scope of the claimed subject matter.

Unless defined otherwise, all technical and scientific terms used herein have the same meanings as commonly understood.

Figure 1:
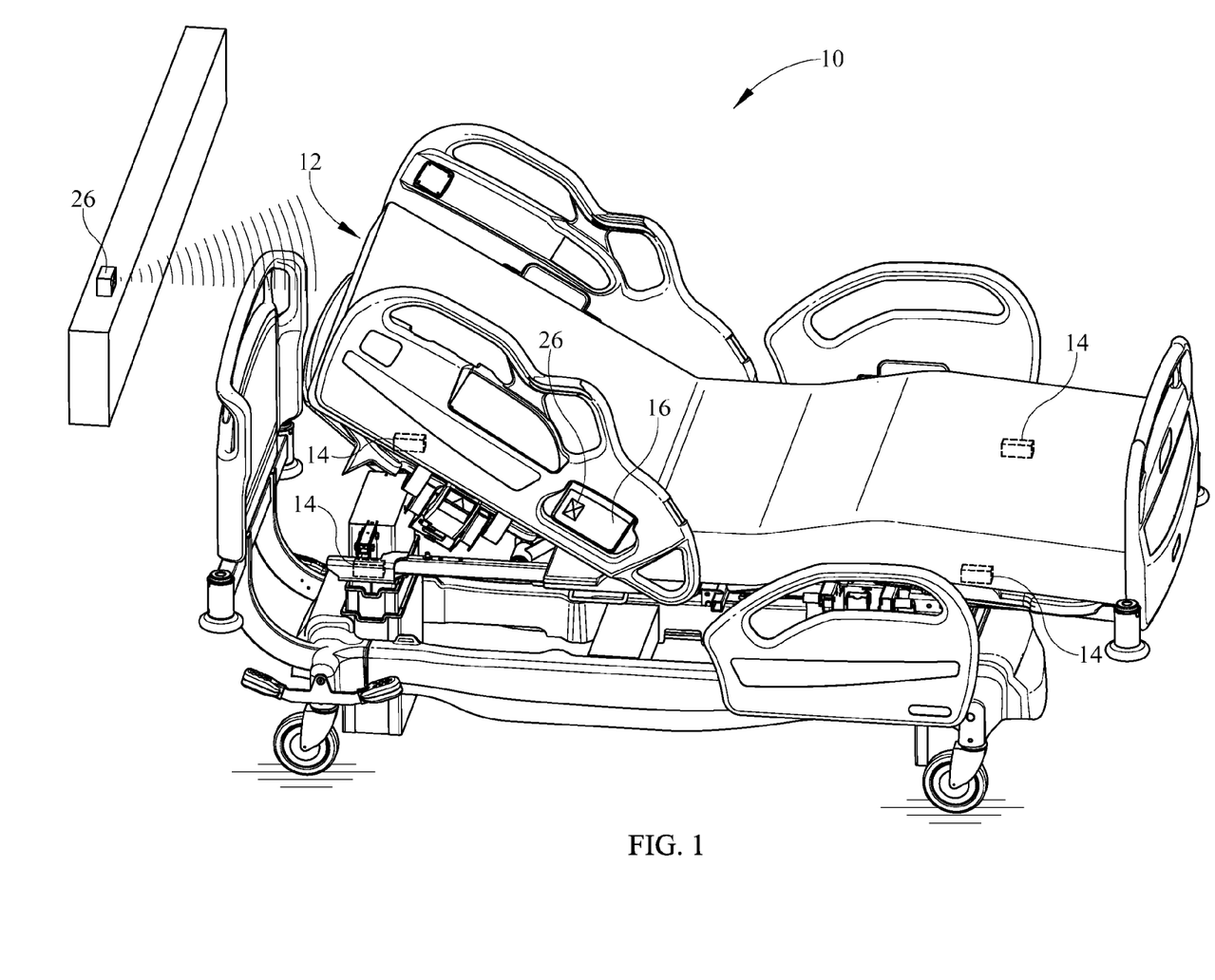
FIG. 1 is a perspective view of one embodiment of the system of the current disclosure, constructed according to principles of the teachings herein.

A person support apparatus 10 according to one illustrative embodiment of the current disclosure is shown in FIG. 1. In one embodiment, the person support apparatus 10 is a hospital bed. In another embodiment the person support apparatus 10 can also be a hospital stretcher, an operating table or other apparatus configured to support a person. The person support apparatus 10 can include a lower frame or base, a plurality of supports coupled with the lower frame, and an upper frame supported on the plurality of supports above the lower frame. The person support apparatus 10 can also include a deck supported on the upper frame. The deck of the person support apparatus 10 can include a head support section supporting head of the person and a foot support section supporting the feet of the person. The deck is configured to further support a person support surface 12 or a mattress 12 as shown in FIG. 1. The person support apparatus 10 includes at least one force transducer 14 to sense the weight supported by said person support apparatus 10 in one embodiment. In another embodiment, at least one force transducer 14 is incorporated with said person support surface 12. The force transducer 14 is in communication with a controller 16 and is a load cell. The force transducer 14 may be any other device capable of converting mechanical forces in to electrical signals, including, but not limited to a potentiometer and a strain gauge. Controller 16 may be any programmable of preprogrammed device capable of receiving at least one control signal or sending at least one control signal. In one embodiment, the person support apparatus control unit serves as the controller 16 as shown in FIG. 1 and in another embodiment the controller 16 may be an independent unit dedicated to operation of the system described herein. At least one motion sensor 26 communicates with the controller 16 and provides the controller 16 information about motion within a predetermined range of distance. In one embodiment a radius of five feet from the motion sensor is the predetermined range of distance, although any other range may be selected. In one embodiment the motion sensor 26 may be integral to the controller 16. In another embodiment, the motion sensor 26 may be integrated in the patient support apparatus 10 or the patient support surface 12. In yet another embodiment, the motion sensor 26 may be placed in any other location in the vicinity of the person support apparatus 10. In one embodiment, the motion sensor 26 may be placed on a head wall.

Motion sensor 26 may be of any type, including but not limited to infrared, ultrasonic, microwave and tomographic types. In one embodiment, a combination of various types of motions sensors 26 is used. Inputs from motion sensors 26 with differing fields of view are weighted differently by the controller 16, thereby allowing for varying sensitivity in different zones in one embodiment. In another embodiment, the motion sensors 26 are calibrated such that certain motion sensors 26 are more sensitive than others. In yet another embodiment, a single motion sensor 26 has differing sensitivity to motion for different zones. In one embodiment, the controller 16 comprises a timer feature, which allows the controller to process signals from the at least one motion sensor 26 for a predetermined time period once the timer is triggered. In one embodiment, the timer feature may be triggered by a predetermined change in weight supported by the person support apparatus 10. The timer feature allows the motion sensor 26 to monitor activity for a predetermined time after it has activated and lack of activity in that time period may be indicative of a fall.

Figure 2:
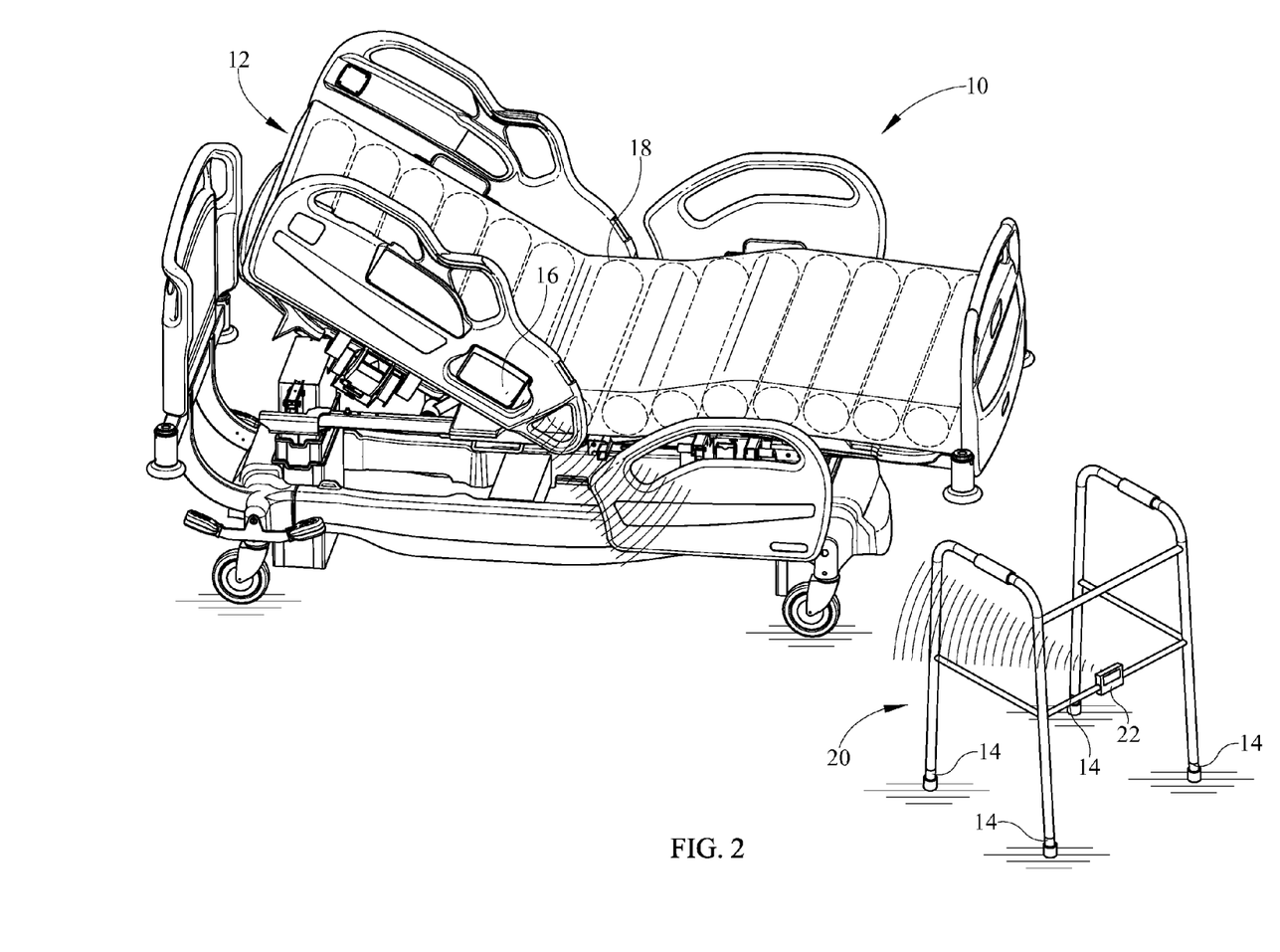
FIG. 2 is a perspective view of another embodiment of the system of the current disclosure, constructed according to the teachings herein.

The illustrative embodiment in FIG. 2 shows a person support surface 12 mounted on a person support apparatus 10. The person support surface 12 comprises at least one bladder 18. In another embodiment, at least one bladder 18 may be incorporated in the person support apparatus 10. Force applied to or removed from the at least one bladder 18 would result in variation of pressure or volume inside the bladder 18. Variation in pressure, volume or density of the medium in the bladder 18 is used by the controller 16 to determine whether or not a person is supported by the person support apparatus 10. In one embodiment, the pressure, volume or density of medium in the unloaded configuration is recorded by the controller 16 and used to determine whether the person support apparatus 10 is supporting a person or is vacant. The controller 16 is in communication with a communication module 22 of a person support device. In one embodiment as shown in FIG. 2, the person support device is a walker 20. The walker 20 has at least one force transducer 14 to determine force applied to the walker 20 and is in communication with the communication module 22. Communication between the controller 16 and the communication module 22 is preferably wireless, although this connection may be wired in another embodiment. Wireless communication between the controller 16 and the communication module 22 may be via any mode, including but not limited to radio frequency communication, blue tooth communication, microwave communication and infrared communication.

Figure 3:
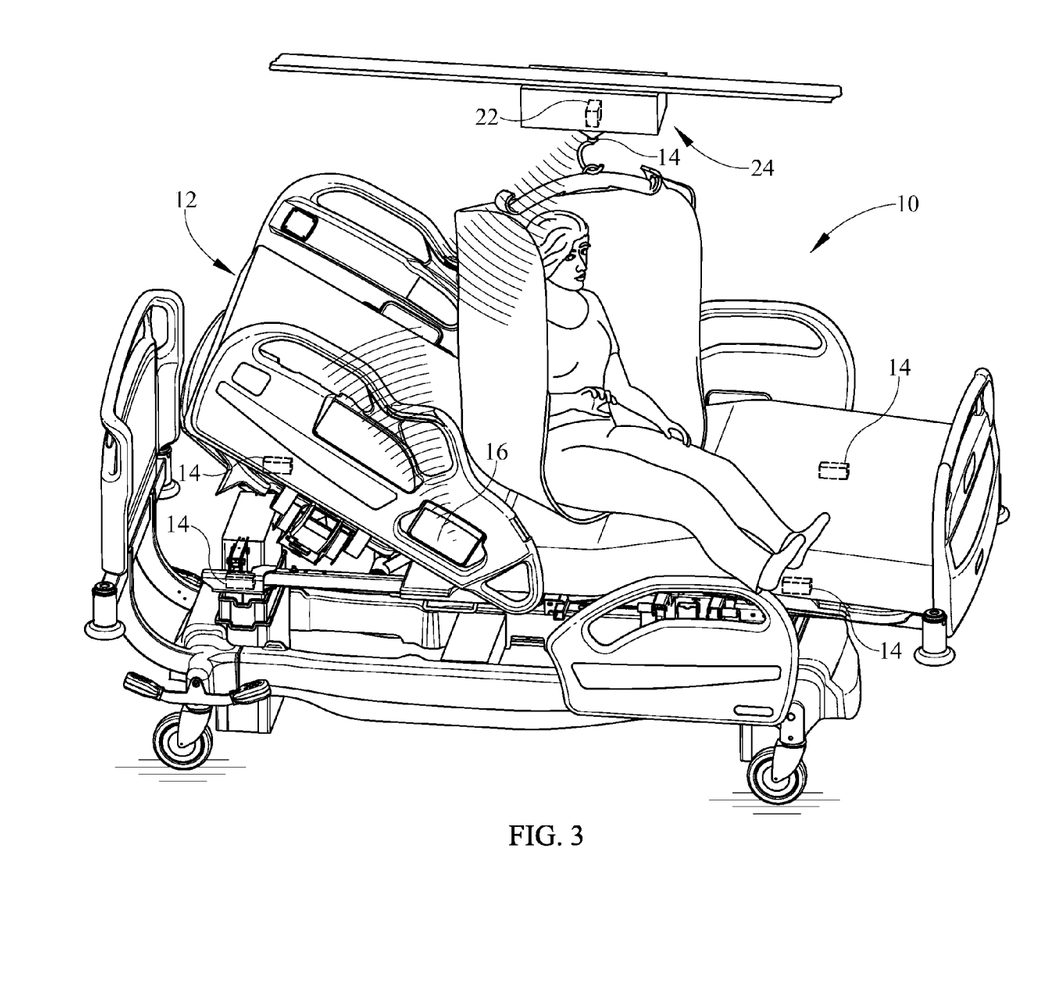
FIG. 3 is a perspective view of yet another embodiment of the system of the current disclosure, constructed according to the teachings herein.

The illustrative embodiment in FIG. 3 shows a person support surface 12 mounted on a person support apparatus 10. The person support apparatus 10 includes at least one force transducer 14 to sense the weight supported by said person support apparatus 10 in one embodiment. In another embodiment, at least one force transducer 14 is incorporated with said person support surface 12. The force transducer 14 is in communication with a controller 16. In another embodiment, variation in pressure, volume or density of medium in the bladder 18 is used by the controller 16 to determine whether the person support apparatus 10 has been loaded or unloaded. The controller 16 is in communication with a communication module 22 of a person support device. In one embodiment as shown in FIG. 3, the person support device is a patient lift system 24. As depicted in FIG. 3, at least one force transducer 14 is incorporated in the patient lift system 24 and is in communication with the communication module 22. In another embodiment, changes in current supplied to and voltage across elements of the patient lift system drive, not shown, may be used to determine change in loading of the patient lift system 24, the drive in communication with the communication module 22. In yet another embodiment, the patient lift system 24 may have a hydraulic or pneumatic drive, in which case, pressure, volume or density are used to determine change in loading of the patient lift system 24, the drive in communication with the communication module 22.

Figure 4:
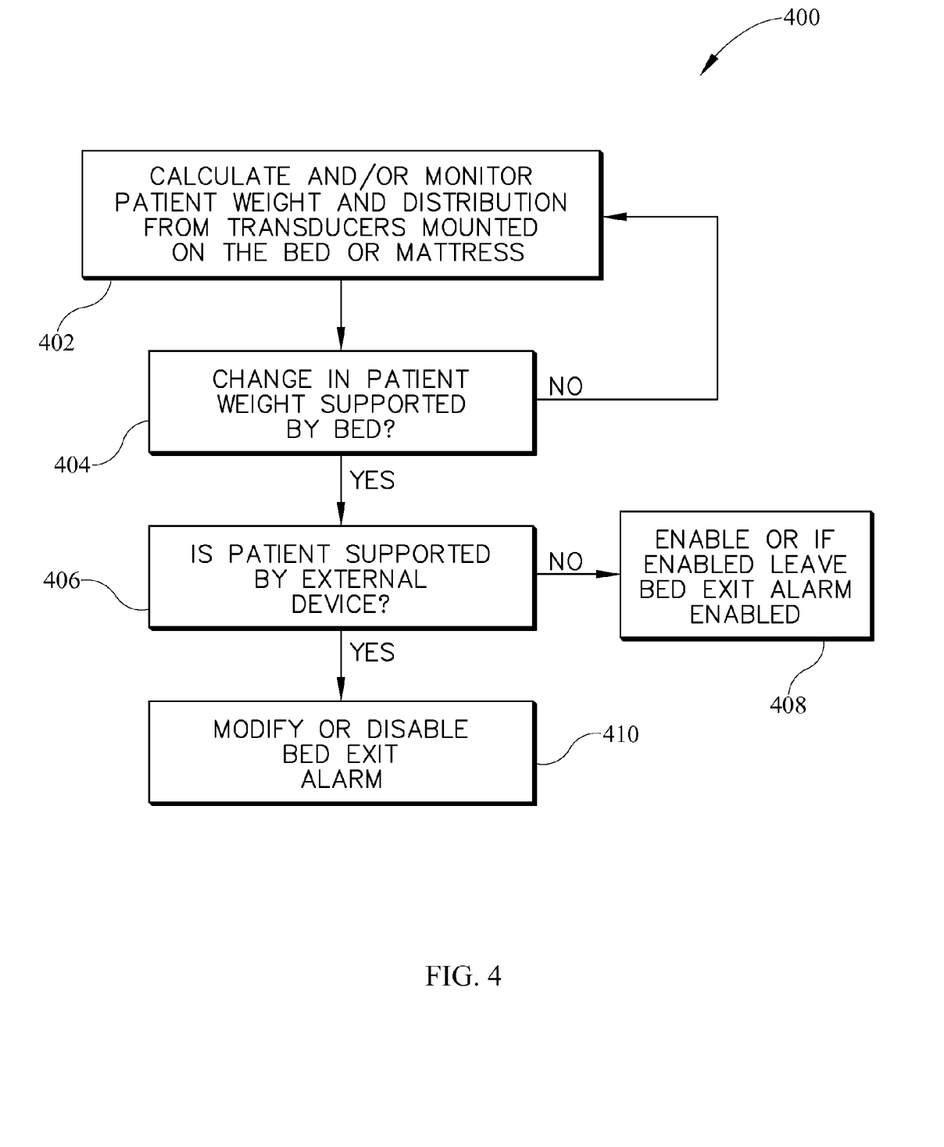
FIG. 4 is a flow chart of operation of the system of the current disclosure in one embodiment, constructed according to the teachings herein.

Flowchart 400 of FIG. 4 shows the operation of the system according to one embodiment. Weight applied on the patient support apparatus 10 is monitored in step 402. In another embodiment weight applied on the patient support surface 12 is monitored in step 402. Change in weight supported by the person support apparatus 10 or the patient support surface 12 is monitored in step 404. If a predetermined change is weight is measured in step 404, it is determined whether a person support device is supporting a predetermined weight in step 406. If the person support device is supporting a predetermined weight, the bed exit alarm is disabled or modified in step 410. In one embodiment, the alarm is muted, and in another embodiment, the alarm is activated in a reduced volume. However, if the person support device is not supporting a predetermined weight, a bed exit alarm is triggered in step 408.

Figure 5:
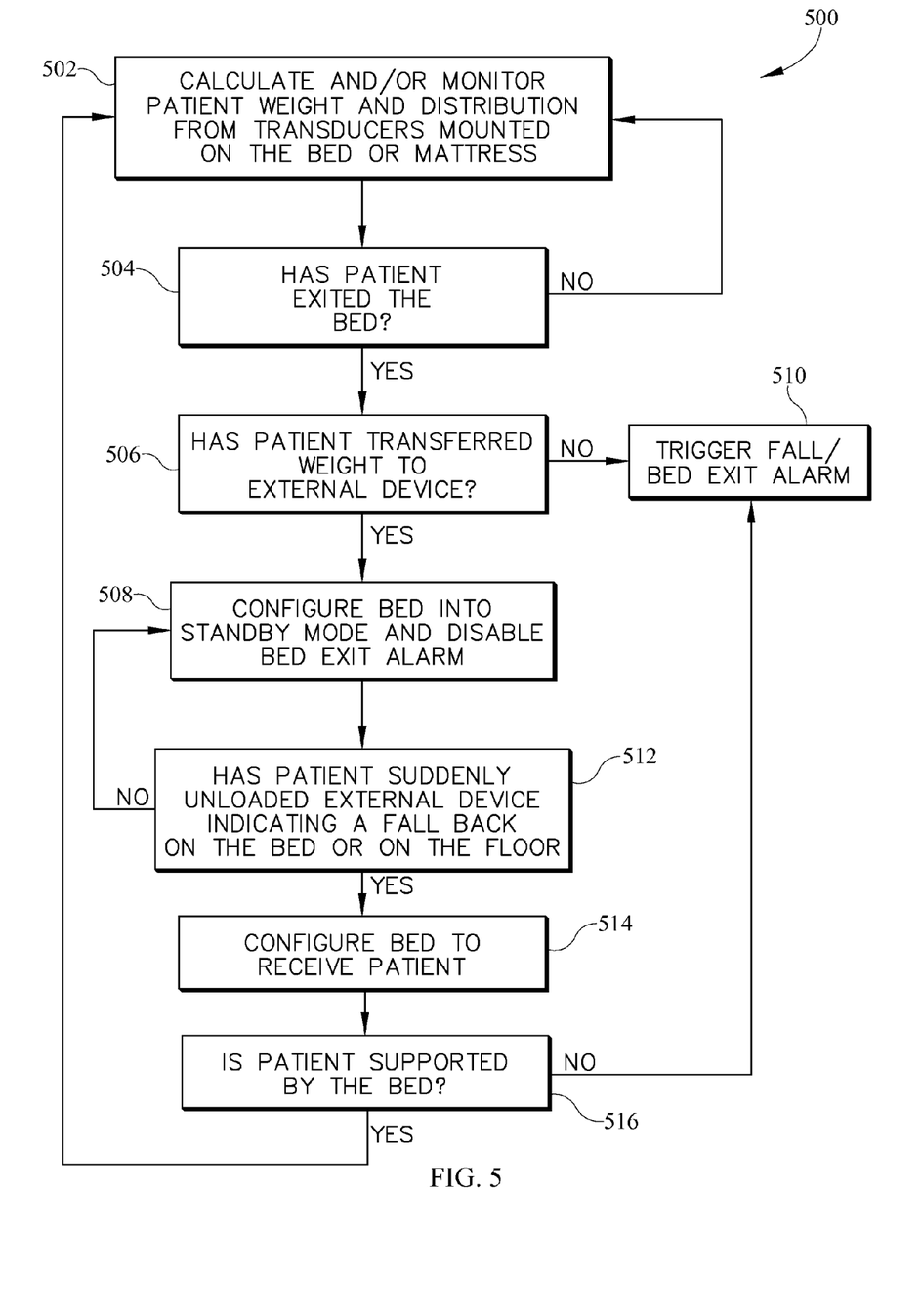
FIG. 5 is a flow chart of operation of the system of the current disclosure in another embodiment, constructed according to the teachings herein.

Flowchart 500 of FIG. 5 shows the operation of the system in another embodiment. Weight supported by the patient support apparatus 10 is monitored in step 502. In another embodiment weight supported by the patient support surface 12 is monitored in step 502. A predetermined change in weight supported by the person support apparatus 10 or the patient support surface 12 is used to determine if a patient has exited the bed in step 504. If a predetermined change in weight supported is measured, it is then determined whether a person support device is supporting a predetermined weight in step 506. If the person support device is not supporting a predetermined weight in step 506, a bed exit alarm is triggered in step 510. However, if the person support device is supporting a predetermined weight, the bed exit alarm is disabled or modified and the patient support apparatus 10 configures in to a stand-by mode in step 508. The stand-by mode comprises a power saving configuration, wherein at least one system on the person support apparatus 10 is powered down to a lower energy consuming state. Weight supported by the person support device is monitored in step 512. If a predetermined reduction in weight supported by the person support device is measured, the person support apparatus 10 is configured to receive the patient in step 514. Unloading of the weight supported by the person support device may be indicative of a fall. The person support apparatus 10 configures to a predetermined configuration to receive the patient, in one case the predetermined configuration is the chair configuration. In another embodiment, pressure or volume inside at least one bladder of the person support surface 12 is varied in step 514 to configure the person support apparatus 10 to receive the patient. Weight supported by the bed is monitored in step 516 to determine whether the patient is now at least partially supported by the person support apparatus 10. If the weight supported by the person support apparatus is less than a predetermined amount, a bed exit alarm is triggered in step 510, indicating that the patient may have fallen from the patient support device and is not supported by the bed. However, if it is determined in step 516 that the patient is supported by the person support apparatus 10, weight supported by the person support apparatus 10 is monitored in step 502.

The system of the current disclosure can be used in numerous other operative embodiments. In one embodiment, information from the force transducers 16 is used by the controller 16 to calculate the center of gravity of the weight supported by the person support apparatus 10 or the person support surface 12. In another embodiment, pressure or volume information of medium inside at least one bladder 18 is used by the controller 16 to calculate the center of gravity of the weight applied. Change in center of gravity of the weight applied is monitored to monitor patient position. Prediction of patient fall or patient egress is made based on the change in location of the center of gravity of the weight supported by the person support apparatus. In another embodiment, distribution of weight supported by the person support apparatus 10 or person support surface 12 is used to predict patient egress or potential patient fall. In one embodiment, predetermined change in center of gravity is used to activate external devices or devices which are a part of the system. In one embodiment, a predetermined change in center of gravity triggers the timer feature described earlier. In another embodiment, a predetermined change in center of gravity activates the motion sensor 26. In yet another embodiment, change in center of gravity of is transmitted to the patient lift system 24 or any other patient support device.

In another operative embodiment of the system, prediction of patient ingress is made when communication between the controller 16 and communication module 22 of a person support device is established indicating proximity of the person support device. In one embodiment, communication with the communication module 22 of a walker 20 indicates that a walker 20 has entered a communication zone, possibly a hospital room. Other information may be transmitted between the controller 16 and the communication module 22. In one embodiment, the controller 16 determines via the communication module 22 that the person support device is bearing weight and therefore a patient is supported by the person support device as opposed to a caregiver operating the system. In one embodiment, signal strength between the communication module 22 and the controller 16 is used to determine the proximity of the person support apparatus 10 with respect to the person support device. In another embodiment, any positioning sensor may be incorporated in the person support device or the person support apparatus 10 to determine the position of one relative to another. A hospital asset tracking system is employed to determine proximity of person support device and the person support apparatus 10 in one embodiment, the person support apparatus in communication with the hospital asset tracking system, not shown, via the communication network 30. The person support apparatus 10 configures to receive a patient when the person support device and the person support apparatus 10 are less than predetermined distance from each other.

Figure 6A:
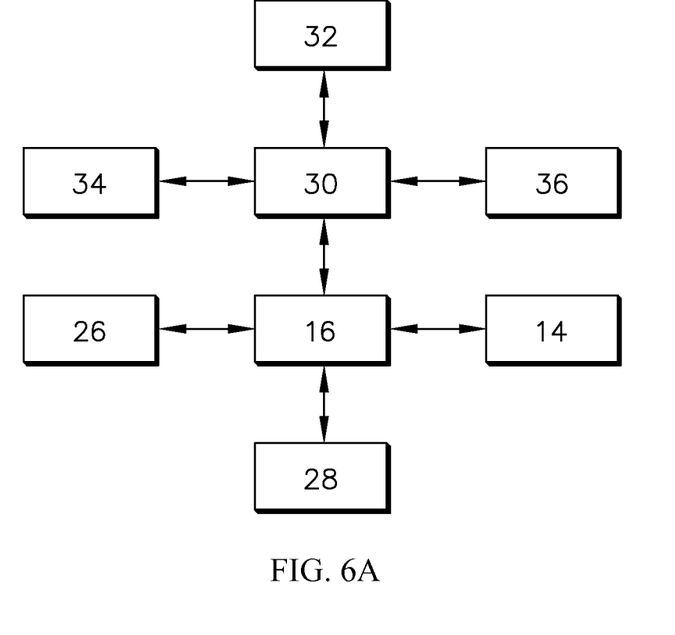
FIG. 6A is a schematic of one embodiment of some elements of the system of the current disclosure, constructed according to the teachings herein.
Figure 6B:
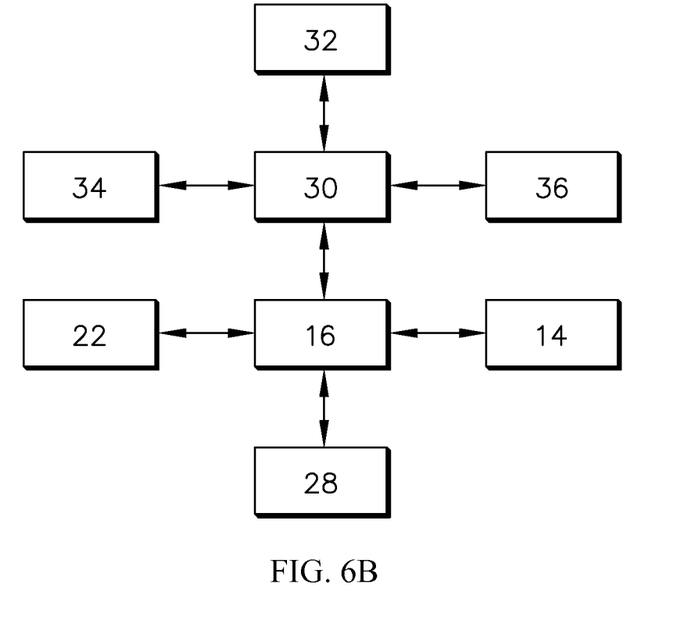
FIG. 6B is a schematic of another embodiment of some elements of the system of the current disclosure, constructed according to the teachings herein.

FIG. 6A and FIG. 6B are schematics showing illustrative embodiments of the current disclosure. FIG. 6A is an illustrative embodiment of the current disclosure wherein at least one motion sensor 26, an alarming unit 28 and at least one force transducer 14 are in communication with a controller 16. The controller is in communication with a communication network 30. The communication network 30 is in communication with at least one Electronic Medical Record (EMR) 36, a hospital communication station 32 and a nurse call system 34. The communication network 30 may be of any type, including but not limited to Wide Area Network (WAN), Local Area Network (LAN), Virtual Private Network (VPN), telephone lines, optical communications, internet communications or telex. FIG. 6B is an illustrative embodiment of the current disclosure where in a communication module 22, an alarming unit 28 and at least one force transducer 14 are in communication with a controller 16. The controller is in communication with a communication network 30. The communication network 30 is in communication with at least one Electronic Medical Record (EMR) 36, a hospital communication station 32 and a nurse call system 34.

The use of the terms "a" and "an" and "the" and similar referents in the context of describing the subject matter (particularly in the context of the following claims) are to be construed to cover both the singular and the plural, unless otherwise indicated herein or clearly contradicted by context. The foregoing description is for the purpose of illustration only, and not for the purpose of limitation, as the scope of protection sought is defined by the claims as set forth hereinafter together with any equivalents thereof entitled to. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

Preferred embodiments are described herein, including the best mode known to the inventor for carrying out the claimed subject matter. Of course, variations of those preferred embodiments will become apparent upon reading the foregoing description. The inventor expects such variations as appropriate, and the inventor intends for the disclosed subject matter to be practiced otherwise than as specifically described herein. Moreover, any combination of the above-described elements in all possible variations thereof is encompassed unless otherwise indicated herein or otherwise clearly contradicted by context.

The disclosures of any references and publications cited above are expressly incorporated by reference in their entireties to the same extent as if each were incorporated by reference individually.

We claim:

1. A system, comprising:
a person support apparatus including a force sensor;
a controller configured to receive signals to determine weight supported by said person support apparatus;
a timer configured to be triggered when weight supported by said person support apparatus decreases
a motion sensor for monitoring activity in a predetermined range of distance away from the person support apparatus; and
an alarm configured to activate when weight supported by said person support apparatus decreases and when activity detected by the motion sensor falls below a predetermined threshold within a predetermined time period beginning when the timer has been triggered by the weight decrease.

2. A system, comprising:
a person support apparatus;
a controller configured to receive signals to determine weight supported by said person support apparatus;
a person support device configured to sense weight supported by said person support device and in communication with said controller; and
an alarm configured to trigger when weight supported by one of said person support apparatus and said person support device changes, and weight supported by the other of said person support apparatus and said person support device does not change by a predetermined amount within a predetermined time period.

3. The system of claim 2, said person support device is a walker.

4. The system of claim 2, said person support device is a patient lift.

5. The system of claim 2 wherein the alarm is configured to be disabled when weight supported by one of said person support apparatus and said person support device changes and weight supported by the other of said person support apparatus and said person support device changes by a predetermined amount within a predetermined time period.

6. The system of claim 5 wherein said person support apparatus further comprises a standby mode which is activated when said alarm is disabled.

7. The system of claim 2, further comprising a hospital communication network in communication with said controller.

8. The system of claim 7, further comprising an electronic medical record system, said controller configured to communicate information to said electronic medical record system.

9. The system of claim 2, further comprising a nurse call system in communication with said controller.

10. The system of claim 2, said person support apparatus configured to receive a user when weight supported by said person support device changes by a predetermined amount.

11. The system of claim 2, said controller configured to determine center of gravity of the weight supported by said person support apparatus.

12. The system of claim 11, said controller configured to predict patient egress or ingress.

13. A method comprising:
monitoring change in weight supported by a person support apparatus;
determining change in weight supported by a person support device; and
activating an alarm when a change in weight supported by one of the person support apparatus and the person support device is detected and weight supported by the other of said person support apparatus and said person support device does not change by a predetermined amount within a predetermined time period.

14. The method of claim 13 wherein in the event that a change in weight supported by one of the person support apparatus and the person support device is detected and weight supported by the other of said person support apparatus and said person support device changes by a predetermined amount within a predetermined time period, modifying said alarm.

15. The method of claim 13, wherein the step of modifying comprises deactivating said alarm.

16. The method of claim 13, wherein in the event that weight supported by the person support apparatus decreases and weight supported by the person support device increases by a predetermined amount within a predetermined time period, configuring said person support apparatus in to a standby mode.

17. The method of claim 13, further comprising the step of configuring said person support apparatus to receive a user if a predetermined decrease in the weight supported by said person support device is detected.

18. The method of claim 17, further comprising the step of monitoring the weight supported by said person support apparatus and activating an alarm if weight supported by said person support apparatus is below a predetermined value.

19. A method comprising:
monitoring change in weight supported by a person support apparatus;
triggering a timer when weight supported by the apparatus decreases by a predetermined amount;
monitoring motion in a predetermined range of distance away from the person support apparatus subsequent to the timer being triggered; and
activating an alarm if the timer has been triggered and if the monitored motion falls below a predetermined threshold during a predetermined time period beginning when the timer was triggered.

20. A system, comprising:
a person support apparatus in communication with a controller, the controller configured to receive signals to determine weight;
a person support device configured to sense weight supported by said person support device and in communication with said controller;
said person support apparatus is configured to receive a user in response to the controller receiving signals indicating that weight supported by said person support device changed by a predetermined amount.

21. The system of claim 20, said person support device is a walker.

22. The system of claim 20, said person support device is a patient lift.

23. The system of claim 20, further comprising an alarm configured to trigger when weight supported by one of said person support apparatus and said person support device changes, and weight supported by the other of said person support apparatus and said person support device does not change by a predetermined amount within a predetermined time period.

24. The system of claim 23 wherein the alarm is configured to be disabled when weight supported by one of said person support apparatus and said person support device changes and weight supported by the other of said person support apparatus and said person support device changes by a predetermined amount within a predetermined time period.

25. The system of claim 24 wherein said person support apparatus further comprises a standby mode which is activated when said alarm is disabled.

26. The system of claim 20, further comprising a hospital communication network in communication with said controller.

27. The system of claim 26, further comprising an electronic medical record system, said controller configured to communicate information to said electronic medical record system.

28. The system of claim 20, further comprising a nurse call system in communication with said controller.

29. The system of claim 20, said controller configured to determine center of gravity of the weight supported by said person support apparatus.

30. The system of claim 29, said controller configured to predict patient egress or ingress.

* * * * *